(12) United States Patent
Wrosz et al.

(10) Patent No.: US 7,572,121 B2
(45) Date of Patent: *Aug. 11, 2009

(54) METHOD AND APPARATUS FOR MASS CUSTOMIZED MANUFACTURING

(75) Inventors: Roman Wrosz, Poway, CA (US); James C. Culp, Pleasanton, CA (US); Craig E. Farren, Livermore, CA (US)

(73) Assignee: Align Technology, Inc., Santa Clara, CA (US)

( * ) Notice: Subject to any disclaimer, the term of this patent is extended or adjusted under 35 U.S.C. 154(b) by 82 days.

This patent is subject to a terminal disclaimer.

(21) Appl. No.: 11/833,806

(22) Filed: Aug. 3, 2007

(65) Prior Publication Data

US 2008/0292741 A1 Nov. 27, 2008

Related U.S. Application Data

(63) Continuation of application No. 10/690,264, filed on Oct. 21, 2003, now Pat. No. 7,261,533.

(51) Int. Cl.
B29C 43/06 (2006.01)
(52) U.S. Cl. .................. 425/110; 425/128; 425/347; 425/384; 425/809
(58) Field of Classification Search ......... 425/110–113, 425/127–129.1, 340–343, 346–348 R, 384, 425/908, DIG. 11, 809
See application file for complete search history.

(56) References Cited

U.S. PATENT DOCUMENTS 3,600,752 A 8/1971 Kopp (Continued)

FOREIGN PATENT DOCUMENTS

CN 1359661 7/2002
DE 19534998 3/1997

OTHER PUBLICATIONS

Adams, Russ, "*Bar Code 1, 2-Dimensional Bar Code Page*," Mar. 11, 2003, 12 pages, http://www.adams1.com/pub/russadam/stack.html, downloaded Nov. 25, 2003.
Mecco Partners LLC, "*Mecco Marking & Traceability, Bumpy Bar Code*", 1 page, http://www.meccomark.com/posicodeorbumpy barcode.asp, downloaded Oct. 11, 2004.

*Primary Examiner*—Yogendra Gupta
*Assistant Examiner*—Thu Khanh T Nguyen
(74) *Attorney, Agent, or Firm*—Klein, O'Neill & Singh, LLP

(57) ABSTRACT

Embodiments of the invention provide a method and apparatus for manufacturing dental aligners. The system includes a workpiece introduction system having at least one workpiece preparation chamber. The system further has a mold manipulation system, having a mold introduction chamber, where a series of different molds may be introduced one after the other; a mold preparation chamber; a workpiece operation chamber; and a mold manipulator to move the mold between the mold introduction chamber, the mold preparation chamber, and the workpiece operation chamber; and a workpiece manipulator to move the workpiece between the workpiece preparation chamber and the workpiece operation chamber. In operation, the method includes steps of inserting a first workpiece into a workpiece preparation chamber; preparing the first workpiece for processing by subjecting the first workpiece to at least one preparation process; moving the first workpiece into a workpiece operation chamber; moving a first mold into a mold preparation chamber; preparing the first mold for processing by subjecting the first mold to at least one preparation process; moving the first mold into the workpiece operation chamber; moving the first mold and the first workpiece into cooperative engagement; subjecting the first workpiece to a vacuum on the side of the first workpiece facing the first mold; and repeating the above steps for a second workpiece and a second different mold.

26 Claims, 8 Drawing Sheets

U.S. PATENT DOCUMENTS

| | | | |
|---|---|---|---|
| 4,295,436 A | 10/1981 | Zangari et al. |
| 4,824,354 A | 4/1989 | Keaton |
| 5,073,329 A | 12/1991 | Carrara |
| 5,259,745 A | 11/1993 | Murayama |
| 5,620,720 A | 4/1997 | Glick et al. |
| 5,847,961 A | 12/1998 | Jones et al. |
| 5,975,893 A | 11/1999 | Chishti et al. |
| 6,210,162 B1 | 4/2001 | Chishti et al. |
| 6,217,325 B1 | 4/2001 | Chishti et al. |
| 6,227,851 B1 | 5/2001 | Chishti et al. |
| 6,299,440 B1 | 10/2001 | Phan et al. |
| 6,309,215 B1 | 10/2001 | Phan et al. |
| 6,394,801 B2 | 5/2002 | Chishti et al. |
| 6,398,548 B1 | 6/2002 | Muhammad et al. |
| 6,406,292 B1 | 6/2002 | Chishti et al. |
| 6,409,504 B1 | 6/2002 | Jones et al. |
| 6,450,807 B1 | 9/2002 | Chishti et al. |
| 6,454,565 B2 | 9/2002 | Phan et al. |
| 6,457,972 B1 | 10/2002 | Chishti et al. |
| 6,463,344 B1 | 10/2002 | Pavloskaia et al. |
| 6,471,511 B1 | 10/2002 | Chishti et al. |
| 6,485,298 B2 | 11/2002 | Chishti et al. |
| 6,488,074 B2 | 12/2002 | Usui |
| 6,488,499 B1 | 12/2002 | Miller et al. |
| 6,497,574 B1 | 12/2002 | Miller et al. |
| 6,499,997 B2 | 12/2002 | Chishti et al. |
| 6,514,074 B1 | 2/2003 | Chishti et al. |
| 6,554,611 B2 | 4/2003 | Chishti et al. |
| 6,572,372 B1 | 6/2003 | Phan et al. |
| 6,582,227 B2 | 6/2003 | Phan et al. |
| 6,582,229 B1 | 6/2003 | Miller et al. |
| 6,602,070 B2 | 8/2003 | Miller et al. |
| 6,607,382 B1 | 8/2003 | Kuo et al. |
| 6,626,666 B2 | 9/2003 | Chishti et al. |
| 6,629,840 B2 | 10/2003 | Chishti et al. |
| 6,633,789 B1 | 10/2003 | Nikolskiy et al. |
| 6,660,209 B2 | 12/2003 | Leyden et al. |
| 6,976,627 B1 | 12/2005 | Culp et al. |

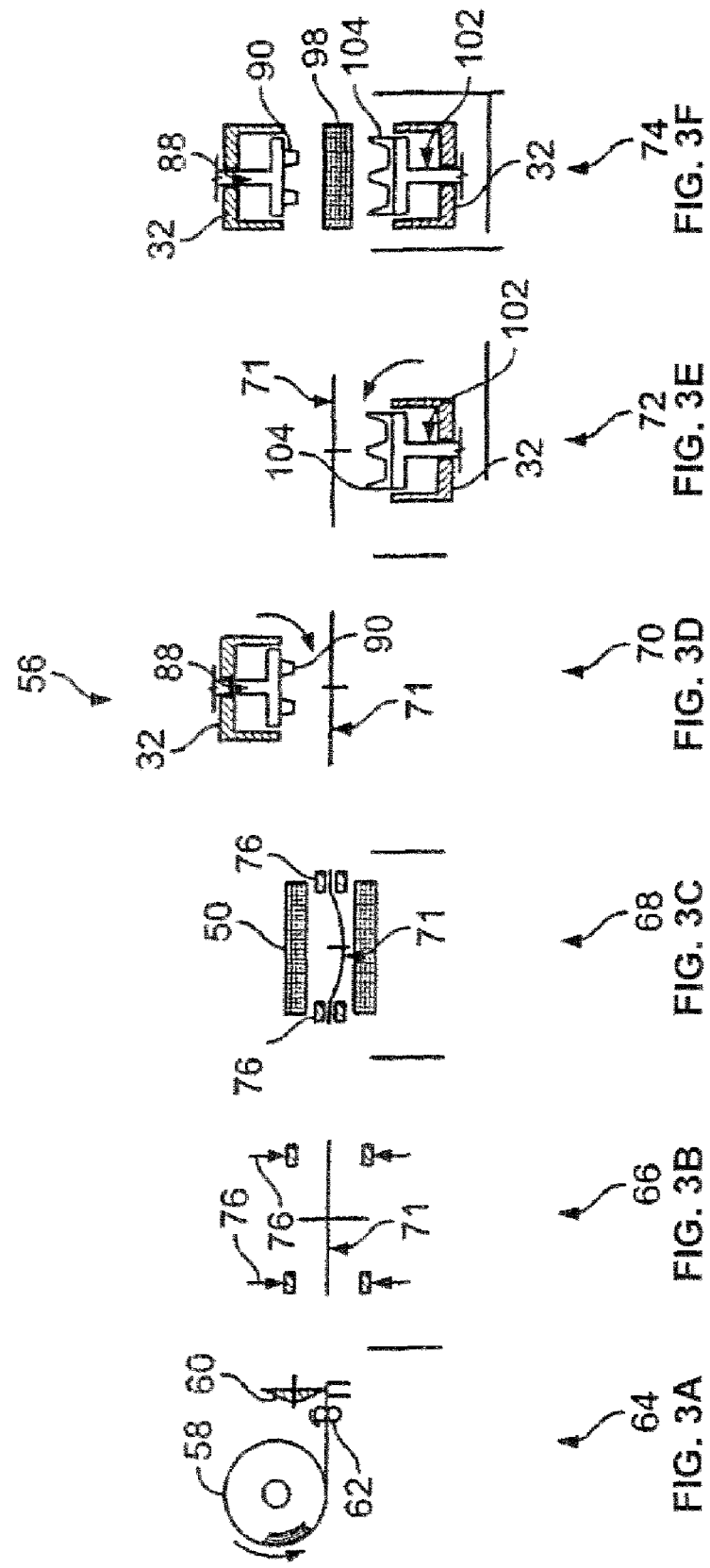

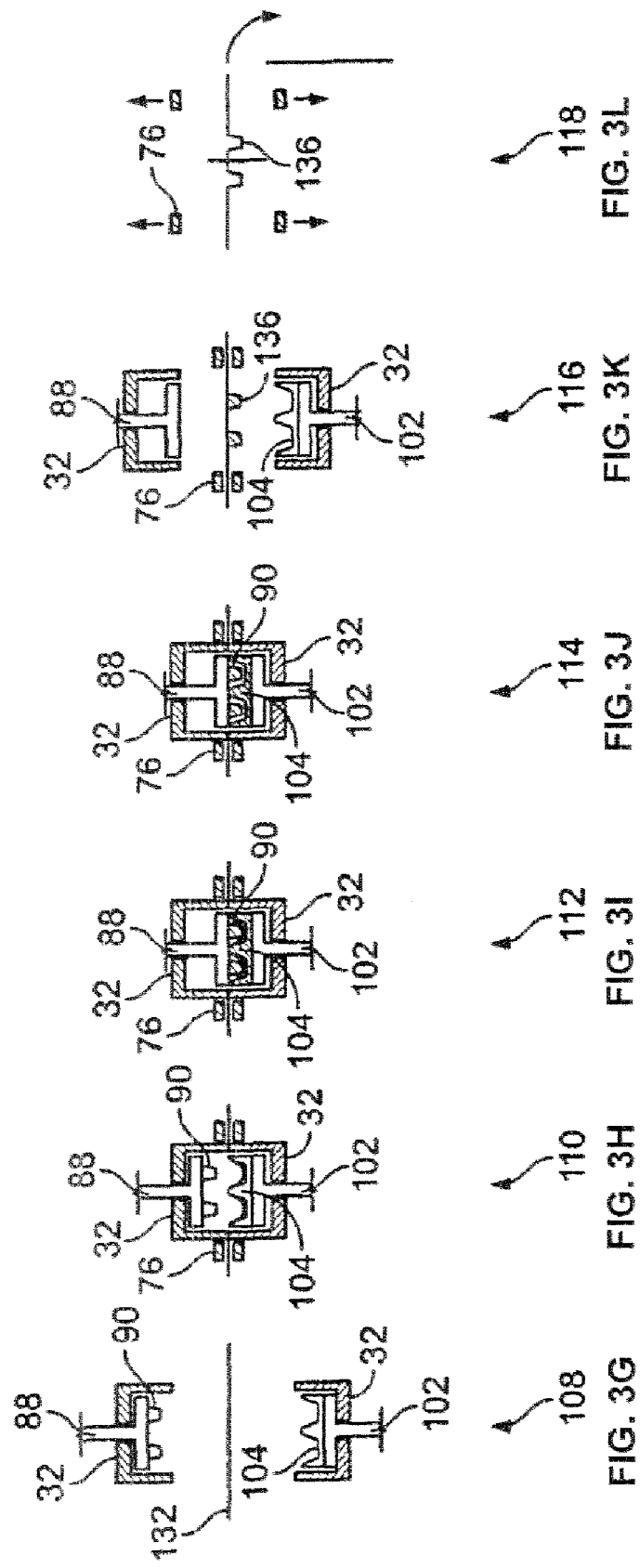

METHOD AND APPARATUS FOR MASS CUSTOMIZED MANUFACTURING

CROSS-REFERENCES TO RELATED APPLICATIONS

This application is a Continuation of application Ser. No. 10/690,264, filed Oct. 21, 2003, now issued as U.S. Pat. No. 7,261,533, the disclosure of which is incorporated herein in its entirety.

BACKGROUND OF THE INTENTION

A. Field of the Invention

This invention relates to the manufacture of mass customized items, and more particularly to automated manufacturing processes of the same.

B. Description of the Related Art

Traditional methods of dental mold making are well known, and include such methods and apparatuses as are described in U.S. Pat. No. 6,497,574, assigned to the assignee of the present application and incorporated by reference herein its entirety.

In such systems, a dental "aligner", for application to a patients teeth, is made from a mold. A series of aligners is constructed which are sequentially applied by the patient to their teeth and which result over time in beneficial changes to the patient's dental structure. The initial mold is made from an impression of the patient's teeth and the subsequent molds and aligners are made using software and a digitization of the initial mold. As described in the patent incorporated by reference above, the initial mold may be constructed by forming an impression of the patient's dentition using a suitable impression material, such as alginate or polyvinylsiloxane (PVS). Impressions of the upper jaw typically include the teeth, the palate and gingival tissue surrounding the teeth on the facial and lingual surfaces. Impressions of the lower jaw typically include the teeth and gingival tissue surrounding the teeth on the facial and lingual surfaces. Plaster is then poured into the impression to form a relief of the dental features. The relief is a permanent, three-dimensional mold of the dentition and oral tissues.

Improved methods of mold making include rapid prototyping. Rapid prototyping is a technology that has developed in the last decade. Through the use of modern solid modeling CAD packages, combined with laser systems and new materials, solid parts may now be generated directly from a computer model. Examples of this technology include stereo lithography (SLA), laminate object manufacturing (LOM), and fused deposition modeling (FDM), to name a few.

Stereolithography is a method that employs an ultraviolet laser to cure a thin layer of liquid plastic into a solid. The process operates by taking a thin layer of the light-sensitive liquid plastic and passing the laser beam over the points where the part is solid. Once a pass is completed, another layer of the liquid is added to the existing part, and the process repeats until the full part height is achieved. SLA parts are extremely accurate, and tend to have excellent surface finishes. A variety of SLA materials are available for different purposes, including waxes, plastics, and flexible elastomers. Typically, an SLA process may produce some 20-25 molds in an hour.

Producing a dental mold with rapid prototyping methods requires the use of a computerized model or digital data set representing the dental geometry and tooth configuration. The model is used to guide the mold making process to produce a replica or relief of the computerized model. The resulting relief is a three-dimensional mold of the dentition. This method of making dental molds is particularly applicable to situations in which multiple molds must be produced. In this case, one computerized model may be used to make a number of molds in an automated fashion. In addition, this method is applicable to situations in which a mold of a tooth arrangement that differs from the patient's current tooth arrangement is needed to be produced or molds of multiple tooth arrangements that differ from each other and the patient need to be produced. In either case, the computerized model of the patient's teeth may be manipulated to portray each new tooth arrangement and a mold may be produced to reflect each successive arrangement. This may be repeated any number of times to derive a number of molds with differing tooth arrangements. Such techniques may speed production time and reduce costs by eliminating the need for repeated casting and artistic resetting of teeth in traditional mold manufacturing.

Series of dental molds, such as those described above, maybe used in the generation of elastic repositioning appliances for a new type of orthodontic treatment being developed by Align Technology, Inc., Santa Clara, Calif., assignee of the present application. Such appliances are generated by thermoforming a thin sheet of elastic material over a mold of a desired tooth arrangement to form a shell. The shell of the desired tooth arrangement generally conforms to a patient's teeth but is slightly out of alignment with the initial tooth configuration. Placement of to the elastic positioner over the teeth applies controlled forces in specific locations to gradually move the teeth into the desired configuration. Repetition of this process with successive appliances comprising new configurations eventually moves the teeth through a series of intermediate configurations to a final desired configuration. For example, a new appliance with a slightly different configuration may be worn for 20 days before replacement with the next appliance in the sequence. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

To carry out such orthodontic treatment, a series of computer models or digital data sets is generated, stored and utilized to fabricate a series of representative dental molds. The fabrication of a series of aligners from such a series of molds involves disposing the molds in a thermoplastic fabrication machine to produce each aligner. The fabrication machine usually relies on selectively hardening a non-hardened resin to produce the appliance or aligner. This fabrication of a series of aligners from such a series of molds requires a significant amount of labor because each mold must be individually hand-inserted and manipulated in the thermoplastic fabrication machine to produce each aligner. This laborious process is operator-intensive and slow as generally only a single workpiece may be fabricated at a time. Other mass-customized manufacturing processes are similarly labor-intensive.

SUMMARY

In one aspect, the invention is directed to an apparatus to manufacture dental aligners, including a workpiece introduction system having at least one workpiece preparation chamber. The system further has a mold manipulation system, having a mold introduction chamber, where a series of different molds may be introduced one after the other; a mold preparation chamber; a workpiece operation chamber; and a mold manipulator to move the mold between the mold introduction chamber, the mold preparation chamber, and the workpiece operation chamber; and a workpiece manipulator to move the workpiece between the workpiece preparation chamber and the workpiece operation chamber.

Implementations of the invention may include one or more of the following. The workpiece introduction system may be an inline system or a rotary turret system. The mold manipulation system may be a rotary turret system. The mold introduction chamber and the mold preparation chamber may be the same chamber. A clamp system may be included to connect the workpiece to the workpiece manipulator. A cutter may be included, whereby an individual workpiece may be removed from a roll of plastic. The workpiece preparation chamber and the mold preparation chamber may include an oven, which may have a preheater or a heater or both. The mold manipulation system may include a plug manipulator to move a plug into the workpiece operation chamber. The apparatus may further include a laser-marking system to mark the workpiece following its removal from the workpiece operation chamber, and a trimming system, such as a multiple-axis CNC system, and preferably a 5-axis one, to trim the workpiece following its removal from the workpiece operation chamber.

In another aspect, the invention is directed towards a method of manufacturing a series of dental aligners. The method includes steps of inserting a first workpiece into a workpiece preparation chamber; preparing the first workpiece for processing by subjecting the first workpiece to at least one preparation process; moving the first workpiece into a workpiece operation chamber; moving a first mold into a mold preparation chamber; preparing the first mold for processing by subjecting the first mold to at least one preparation process; moving the first mold into the workpiece operation chamber; moving the first mold and the first workpiece into cooperative engagement; subjecting the first workpiece to a vacuum on the side of the first workpiece facing the first mold; and repeating the above steps for a second workpiece and a second different mold.

Implementations of the method may include one or more of the following. The preparation of the first or second workpiece mal include preheating or heating the first or second workpiece, respectively. This heating may occur at a temperature of between about 525 and 595° F. The same is true for the first or second mold. The method may further include moving a plug and the first workpiece into cooperative engagement. The method may further include marking the workpiece, such as by a laser-marking device, or trimming the workpiece.

BRIEF DESCRIPTION OF THE DRAWINGS

In the drawings, which illustrate embodiments of the present invention and are not intended to be limiting:

FIGS. 3A-3L are stepwise schematic views showing an embodiment of a manufacturing method in accordance with the principles of the invention.

DETAILED DESCRIPTION

Although hereinbelow are described what are at present considered the preferred embodiments of the invention, it will be understood that the invention can be embodied in other specific forms without departing from the spirit or essential characteristics thereof. The present embodiments are, therefore, to be considered in all aspects as illustrative and not restrictive. Accordingly, the invention is limited solely by the claims appended hereto.

Figure 1:
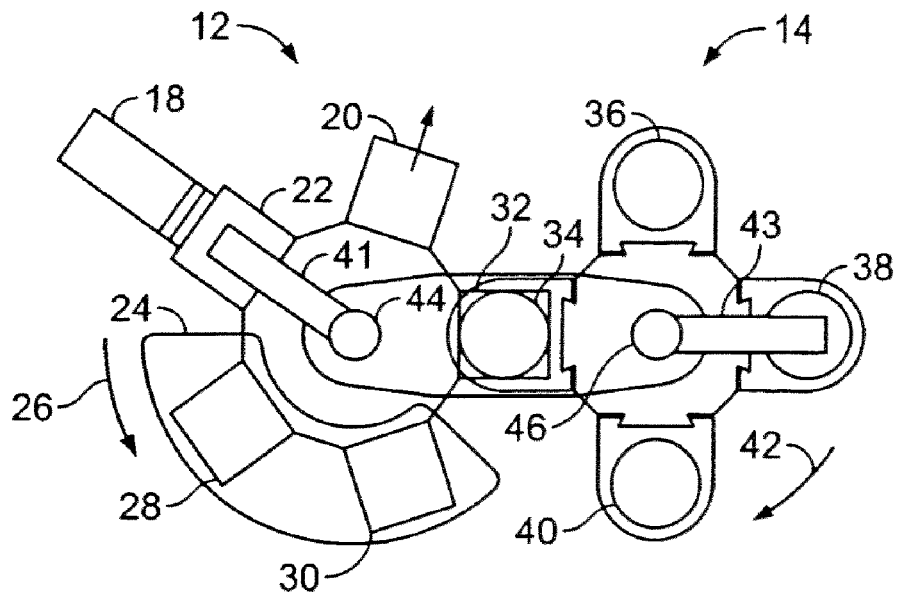
FIG. 1 is a top schematic view of a first embodiment of an automated manufacturing apparatus constructed in accordance with the principles of the invention.

Tuning now to the drawings, in which similar reference characters denote similar elements throughout several views, FIG. 1 illustrates one embodiment of a manufacturing apparatus constituting an embodiment of the invention. In particular, FIG. 1 shows a workpiece introduction system in which thermoplastic workpiece preparation and introduction are accomplished via a rotary turret apparatus. A rotary "plastic" turret 12 is in cooperative engagement with a mold manipulation system, here mold turret 14. The plastic turret 12 rotates about a plastic turret axis 44 and the mold turret 14 rotates about a mold turret axis 46. In general, and as will be described in greater detail below, the plastic turret 12 provides various preparatory functions for a plastic initially sheet-shaped workpiece 71 (see FIG. 3) and the mold turret 14 provides the shaping of the workpiece 71 into a formed or finished aligner using the mold.

The plastic turret 12 has various workpiece preparation chambers to perform sequential processing functions in a semi-continuous fashion. These chambers include a proximal loading chamber 18 for introduction of workpieces. In this chamber, each workpiece 71, which may have been previously clamped to a cartridge or other clamping system or the like to facilitate its convenient introduction and manipulation, is placed on a workpiece manipulator 41 for introduction into and manipulation within the plastic turret 12. The workpiece 71 then enters the rotary portion of the plastic turret 12 via a distal loading chamber 22. The plastic turret 12 rotates in the direction indicated by a plastic turret direction of rotation 26, which moves the workpiece 71 into the next processing chamber. The workpiece 71 may be heated via an oven 24, the same including a preheater 28 and a heater 30. For example, the temperature of the workpiece 71 may reach 525 to 595° F. in the preheater 28 and about the same or higher in the heater 30. This heating allows the workpiece 71 to become pliable and subject to formation via a mold and plug.

After departure from the heater 30, the heated workpiece 71 enters the workpiece operation chamber 32 of the mold turret 14. This position of cooperative engagement with the workpiece operation chamber 32 is indicated in FIG. 1 by a reference numeral 34. There it cooperatively engages a mold and plug, the function and operation of which is described below. Once the heated plastic workpiece 71 is formed by the mold and plug, the same enters an ejection chamber 20, where it may be separated from the mold, marked and trimmed by a process further described below. In particular, the ejection chamber 20 is generic for a group of systems that may include further processing, marking, trimming, etc.

The mold turret 14 also has various chambers to perform various functions, and rotates in the direction indicated by a mold turret direction of rotation 49 to allow sequential processing in a semi-continuous fashion. These chambers include a mold-loading chamber 36, a plug-loading chamber 38, the workpiece operation chamber 32, and a mold-preheating chamber 40. The mold may be moved between these chambers via a mold manipulator 43. The mold manipulator 43, which may have a actuator shape to accomplish up-and-down movements, may also be moved such that the mold is in cooperative engagement with a workpiece 71 in the workpiece operation chamber 32. The details of the cooperative engagement and fabrication process are described in greater detail below with regard to FIG. 3.

Figure 2:
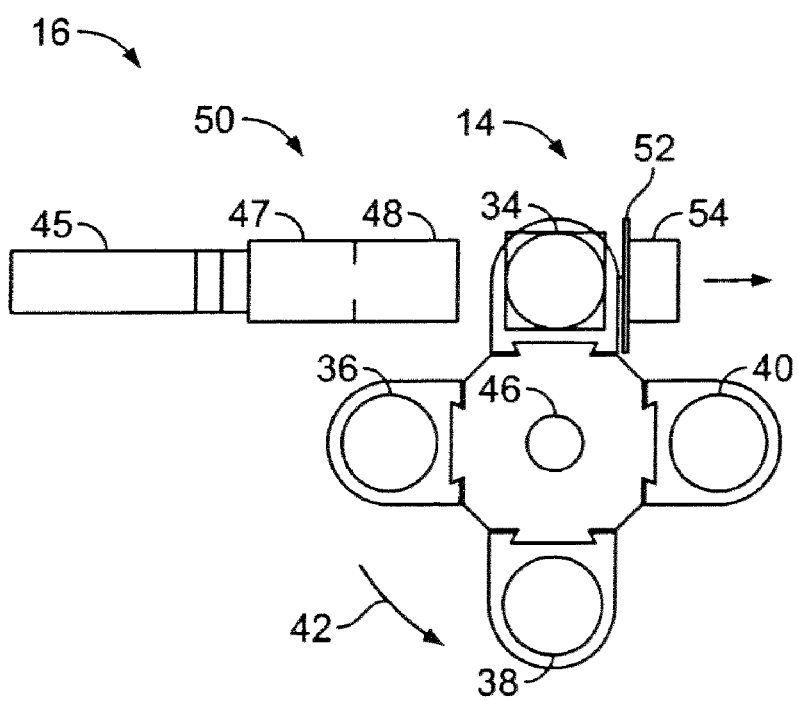
FIG. 2 is a top schematic view of a second embodiment of an automated manufacturing apparatus constructed in accordance with the principles of the invention.

FIG. 2 is a top schematic view of a second embodiment of an automated manufacturing apparatus constricted in accordance with the principles of the invention. FIG. 2 shows an inline plastic workpiece preparation system 16 in cooperative engagement with the mold turret 14. As in FIG. 1, in general, the inline plastic workpiece preparation system 16 provides various preparatory functions for the workpiece 71 and the mold turret 14 performs the shaping of the workpiece 71 into a formed aligner using a mold. The basic construction of the mold turret 14 in FIG. 2 is similar to or the same as that of the mold turret 14 in FIG. 1, and the discussion of the mold turret 14 is correspondingly the same as that above.

The inline plastic workpiece preparation system 16 has various chambers to perform various functions. An inline loading chamber 45 is provided in-line with an inline oven 50. The inline oven 50 may include an inline preheating chamber 47 and an inline heating chamber 48.

The inline system has certain advantages over the rotary system of FIG. 1. For example, in the inline system, a roll of plastic may be conveniently employed to provide the basic workpiece material, and this roll can be cut into individual workpieces 71 at any time during the fabrication process, including even after the workpiece 71 is formed into a finished aligner 136. In this way, the system may take advantage of assembly line techniques and have each station require nearly the same amount of time, such that each workpiece is worked seriatim. By contrast, in the rotary system, each workpiece 71 must be cut into an individual piece, at the latest, by the time the workpiece 71 enters chamber 20.

Also shown in this embodiment, but which may also be in any other embodiments, is a marking system 52 and a trimmer 54. The marking system 52, such as a laser marking system, may be used to burn a predetermined code onto the workpiece 71. The predetermined code may be used to identify the workpiece 71 during use, as it is important for the user to be able to choose the appropriate aligner for use during the dental therapy. The predetermined code corresponds to the mold used to form the aligner, and is further correlated to the NC file created by the initial digitization and software analysis of the patient's teeth.

The trimmer 54 removes the excess plastic from the aligner 136, and is typically a 5-axis CNC (computer-numerical-control) machine. Generally, a 5-axis machine is used although in some circumstances less may be employed. The CNC machine reads data from the NC file corresponding to the aligner, this NC file generated as noted above by the initial three-dimensional digitization and subsequent software analysis.

After the plastic is trimmed, the mold is removed from the finished workpiece or aligner 136. This step generally requires human intervention, as the removal process is particularly difficult to achieve via automation. However, in some instances, this may also be performed. To assist in the removal, the mold and/or the aligner may be made with a release agent so as to ease separation. Such release agents may be, e.g., soap, Teflon®, or silicon, or other similar agents.

Figure 4:
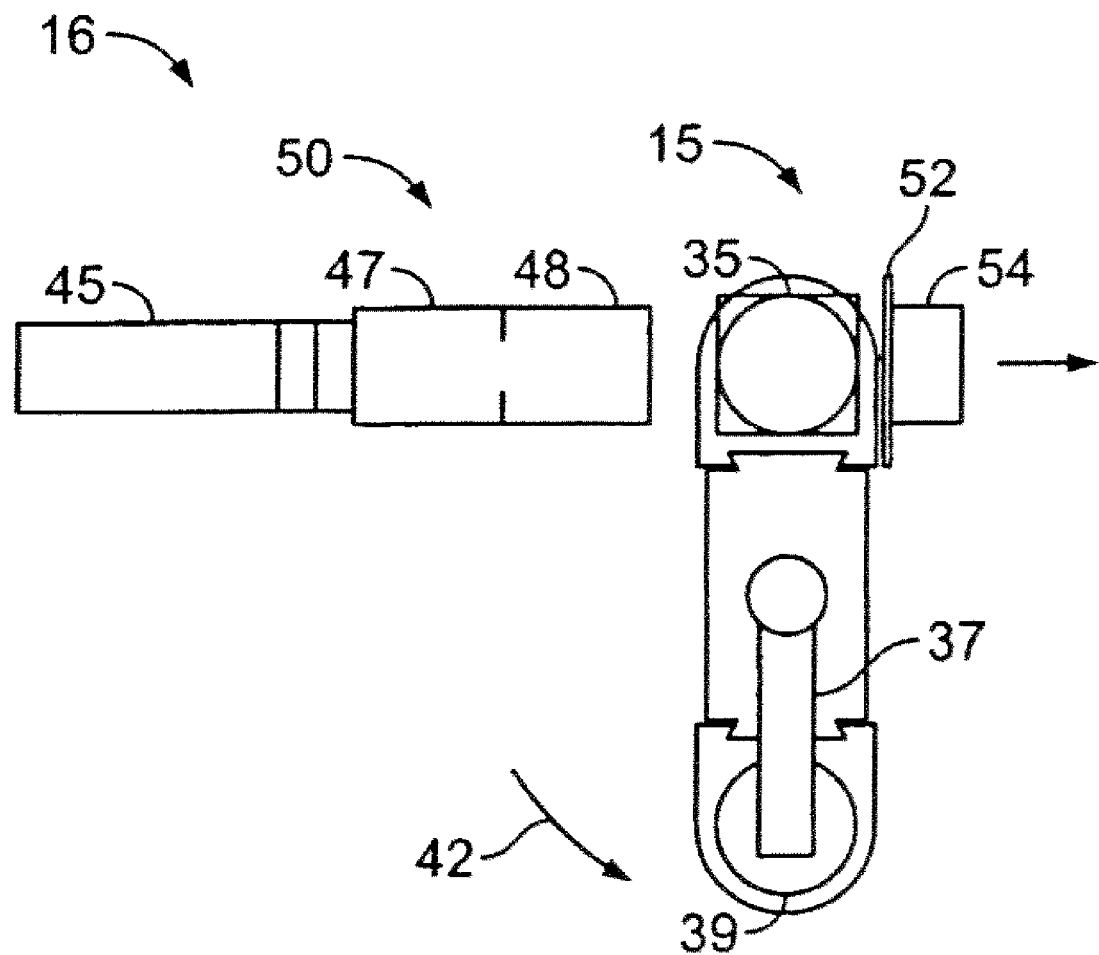
FIG. 4 shows a top schematic view of a third embodiment of an automated manufacturing apparatus constructed in accordance with the principles of the invention.

In another implementation, as shown in FIG. 4, an inline plastic workpiece preparation system 16 is used in combination with a modified mold turret 15. In the modified mold turret 15, a single chamber 39 is used for mold introduction and preparation and a mold manipulator 37 transfers the mold from the chamber 39 to the workpiece operation chamber 35. This embodiment has the advantage of convenience and simplicity. The remainder of the system may be as previously described.

In use, and also referring to FIGS. 3A-3L, which illustrate stepwise schematic views showing an embodiment of a manufacturing method in accordance with the principles of the invention, a plastic sheet from a roll 58 may emerge through a set of rollers 62 (FIG. 3A, step 64), the plastic sheet later to be cut by a cutter 60. After cutting, the cut sheet, now termed a "workpiece 71", is grasped by a set of clamps or clamping system 76 so that the workpiece 71 may be held securely for further processing (FIG. 3B, step 66). Following clamping, the workpiece 71 may be subjected to preheating by an oven 50 (FIG. 3C, step 68). The heating allows the workpiece 71 to be made more pliable and thus easier to work.

Following preheating, the workpiece 71 is moved into a workpiece operation chamber 32 via a workpiece manipulator such as is shown in FIG. 1. The workpiece operation chamber 32 includes two holes such that two opposing actuators may pass therethrough. A mold actuator 88 is employed to support a mold 90 and a plug actuator 102 is employed to support a plug 104. The mold actuator 88 may be integral with the mold manipulator 43 or they may be entirely separate systems.

The workpiece 71 is moved into proximity of the mold 90 (FIG. 3D, step 70) and the plug 104 (FIG. 3E, step 72), see FIG. 3G, step 108. A separate heater 98 may be employed to preheat each of the mold 90 and the plug 104 (FIG. 3F, step 74). The workpiece operation chamber 32 may be heated such that the workpiece 71 becomes even more flexible and pliable (FIG. 3H, step 110). The mold 90 and the plug 104 may be brought into cooperative engagement by action of the mold actuator 88 and the plug actuator 102 (FIG. 3I, step 112). The plug 104 helps to ensure that the plastic of the workpiece is pulled over the mold. A vacuum may then be brought to bear on the workpiece 71, on the side of the workpiece 71 opposite that of the plug 104, such that the workpiece 71 achieves an even greater and tighter fit to the mold 90 (FIG. 3J, step 114). After the workpiece 71 has achieved the same shape as the mold 90, the mold actuator 88 and the plug actuator 102 may be separated, at which point the mold 90 may be separated from the mold actuator 88 and may fit within the formed workpiece (FIG. 3K, step 116). The mold 90 may be separated from the workpiece 71 by the action of an air actuator (FIG. 3L, step 118). The clamps 76 may be removed.

The finished workpiece, now an aligner 136, may be marked for identification as described above and trimmed to remove excess plastic also as described above. The aligners or appliances will be marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Figure 5:
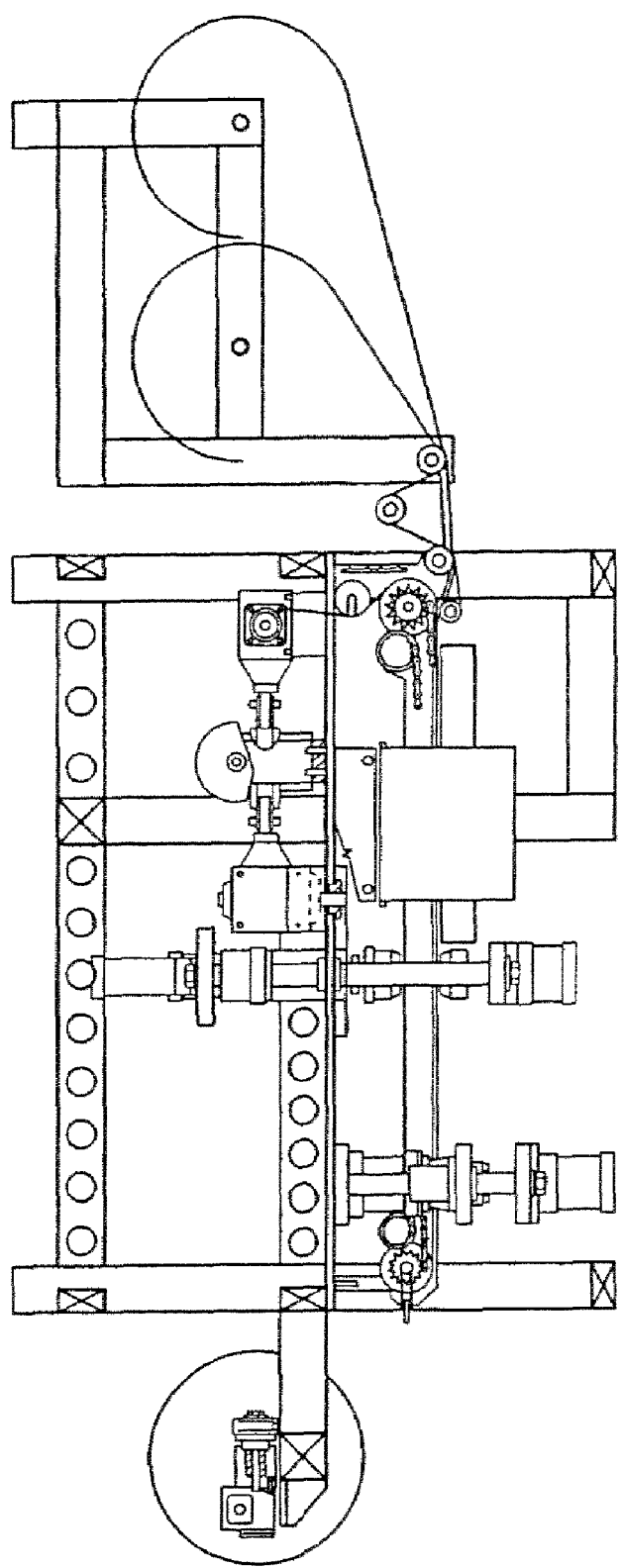
FIG. 5 shows a cross-sectional view of one embodiment of a mass-customized manufacturing system.
Figure 6:
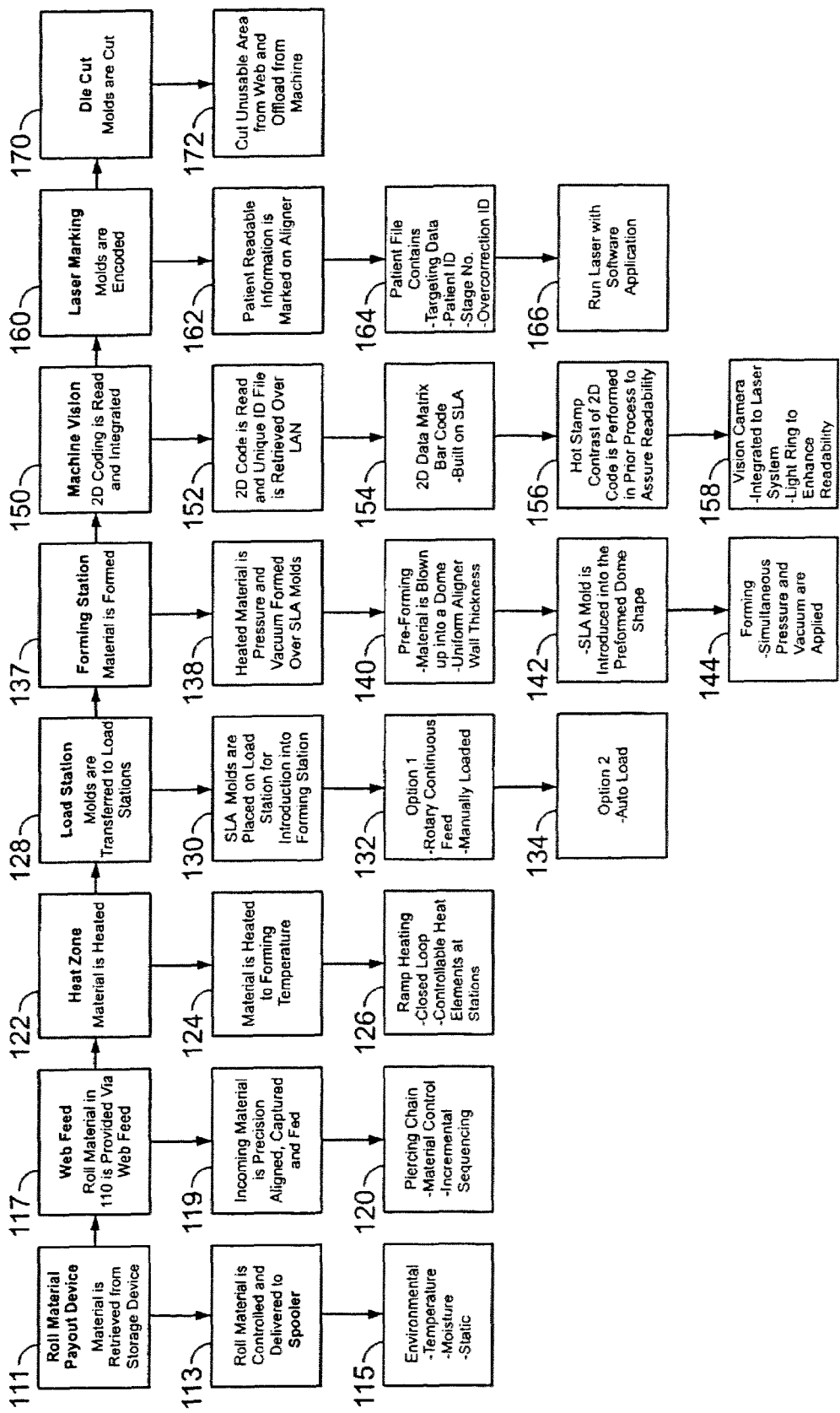
FIG. 6 shows a process for performing mass-customization using the machine of FIG. 5.

FIG. 5 shows a cross-sectional view of one embodiment of a mass-customized manufacturing system, while FIG. 6 shows a process for performing mass-customization using the machine of FIG. 5. In the implementation of FIG. 5, the apparatus for fabricating a mass-customized appliance includes a web feeder; a load station coupled to the web feeder to receive a mold; and a forming station coupled to the load station to generate the appliance. A programmable logic controller (PLC) is used to control the forming station. The PLC controls electrical and pneumatic I/O for the web feeder, heat zone, rotary SLA feed, forming, machine vision and die cutting functions. The PLC stores and retrieves multiple recipes to perform its tasks. The PLC communicates over a network to allow real time monitoring of production throughput, preventive maintenance, and remote diagnostics management. The web feeder provides an in and out-feed to a piercing chain to provide safe rapid recovery from both machine malfunctions and roll change out. A heater provides a heat zone over the web feeder. The heat zone further comprises a plurality of in-line individually controlled modular ceramic heaters. The load station comprises an opposing dual platform to allow continuous rotary introduction of unique molds to web without interruption to the process. The load station allows simultaneous loading of the next mold during the forming process. The forming station allows continuous introduction and removal of new unique mold to be thermoformed at each cycle. The forming station further comprises a pressure/vacuum chamber and wherein the pressure/vacuum chamber is first sealed on the web to allow pre-forming. The mold is introduced to the pre-formed web and simultaneously the vacuum and pressure are applied to form the material on the mold. The material is blown in a first direction over the mold and then blown in an opposite direction to deposit over the mold. Each mold is formed with a 2D data matrix code containing unique identification of the mold. A machine vision module performs a data acquisition from a multi-dimensional matrix code and reports it to a laser marking system. The vision module comprises a camera and a light ring set up vertically over the station. The chamber is opened the load platform is withdrawn and the mold is retained in the web and transferred to the machine vision module. The laser marker is a diode pump laser with marking head, standard marking and targeting software and laser parameters. The PLC and PC controller provide HMI safety access and the laser system meets CDRH certification by manufacturer.

In one embodiment, an integrated thermo-former and laser marker device supports mass customization manufacturing of dental appliances. The system includes in-line integration of: Incremental Web precision feed and speed control; multiple heat zone control and closed loop monitoring capable of ramping material to forming temperature; and continuous feed rotary SLA mold introduction to the web forming process. The thermoform process incorporates the web, a unique mold every cycle, pre-forming the web, pressure and vacuum forming, and mold retention in the web. A machine vision station acquires data that identifies each unit and communicates the data to the laser marker. The laser marker retrieves unit ID data over a network and performs automated targeting of a marking zone. A die cutter automatically removes a predetermined area of usable web and discharges the unit to an automated material handling equipment. A Web out feed take-up spool is used to manage waste material.

In one embodiment, a programmable logic controller (PLC) manages electrical and pneumatic I/O for the web feed, heat zone, rotary SLA feed, forming, machine vision and die cutting functions. The PLC can store and retrieve multiple recipes. The PLC also communicates using network connectivity to allow real time monitoring of production throughput, preventive maintenance, remote diagnostics management and downtime.

In one aspect, the web feed is capable of handling a pliant material such as plastic. The web feed interacts with a payout device that controls environmental and static control to meet the requirements for the material. An In and Out-feed provides a piercing chain mechanism to provide a rapid roll change out.

In another embodiment, in-line individually controlled modular ceramic heaters are used in the heat zone. Ceramic heaters with controlled zones are used to achieve required cycle times. An opposing dual platform load station allows continuous rotary introduction of unique molds to the web without interruption of the process. This will allow simultaneous loading of the next mold during the forming process. The forming station allows continuous introduction and removal of new unique mold to be thermoformed at each cycle. The pressure/vacuum chamber is first sealed on the web allowing pre-forming to occur. The mold is then introduced to the pre-formed web, and simultaneously the vacuum and pressure are applied to form the material on the mold. As the chamber is opened, the load platform is withdrawn, and the mold is retained in the web and transferred to the machine vision station.

Every unit, in this case a stereolithography apparatus (SLA) mold, is built with a 2D data matrix code containing unique identification. Machine vision performs a data acquisition from that data matrix code and reports the data to the Laser Marking station. The vision system includes a digital camera and light ring set up vertically over the station. During laser marking, a computer-controlled laser with marking head receives data from the machine vision system. The laser machine interlocks to provide safe access for maintenance, minor repairs or adjustments to equipment.

FIG. 6 shows an exemplary process to fabricate units using mass-customization. First, rolled thermoplastic material is retrieved from a storage device 111. The rolled material is controlled and delivered to a spooler 113. At this stage, the material is in a controlled environment that keeps temperature, moisture and static electricity conditions, among others, within a predetermined tolerance (115). Next, the rolled material is provided to a web feed system 117. Incoming material is precision aligned, captured and fed (118). The material is also provided to a piercing chain for incremental sequencing control (120). The web fed thermoplastic material is provided to a heat zone where the material is heated in one embodiment (112). The material is heated to a forming temperature (124). A ramp heating system is used with controllable heat elements (126).

The molds 90 are transferred to a load station (128). The molds are first placed on a load station for introduction to a forming station (130). The molds can be manually loaded (132) or can be automatically loaded (134). Next, the thermoplastic material is formed over one or more molds (137). The heated material is pressure and vacuum formed over the molds (138). In a pre-forming operation, material is blown into a dome shape to provide a uniform thickness (140). The mold is introduced into the pre-formed dome shape (142), and pressure and vacuum is applied to form the unit (144).

The formed material includes part identification (ID), which is detected by machine vision using a camera and light ring (150). A 2D ID code is read and a corresponding file for the unit is retrieved over the network (152). The 2D data matrix bar code is formed directly on the unit (154). A hot-stamp contrast of the 2D code is performed to improve read-ability (156). The output of the vision camera with light ring is communicated for marking purposes (158).

Figure 7:
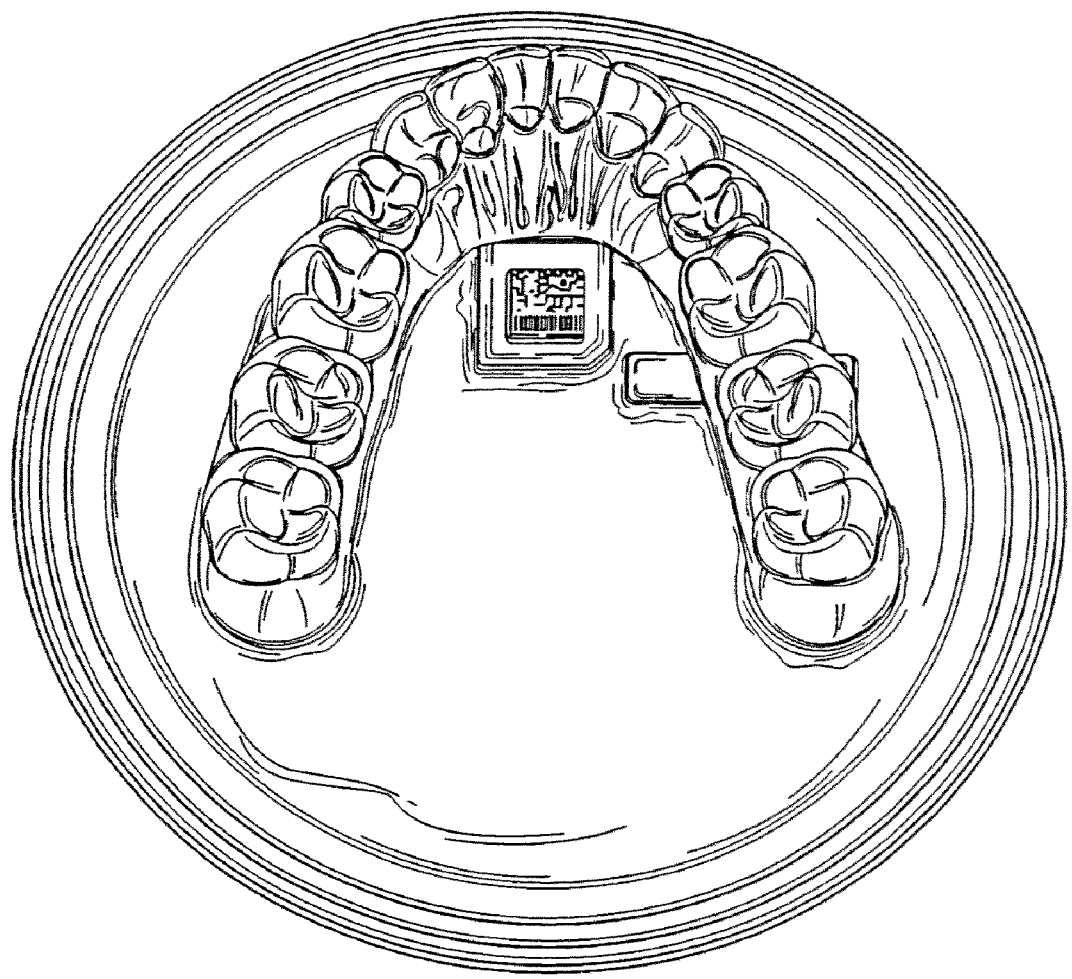
FIG. 7 shows an exemplary dental appliance during manufacturing.

The identification information is provided to the laser marker (160), where the units are encoded. In the case of dental appliances, patient readable information is marked on each appliance (162). The data file for one dental embodiment includes patient ID, stage, and overcorrection ID, for example (164). A laser then burns the patient readable information on the appliance (166). FIG. 7 shows an exemplary dental appliance during manufacturing at operation 166. Subsequently, the units are die cut and trimmed (170). Unused material is off-loaded from the system (172).

After trimming, the aligner 136 is provided to a tumbler. In one embodiment, the tumbler is a centrifugal barrel finishing tumbler. In one embodiment, a turret with four barrels mounted parallel to its axis such as the CPC2500 from United Finishing System Inc. (Baldwin Park, Calif.) is used. Small pebbles are placed therein to polish the parts. In one embodiment, the pebbles are triangular-shaped pebbles. When the turret rotates, the barrels are driven at a 1:1 ratio in the opposite direction of rotation maintaining a stationary orbit around the center hub (similar to the action of a Ferris wheel). The resulting gravitational force generates friction on the contents within the barrel. The parts are forced through the media in a cyclonic action to deburr, refine and polish at high speed. Aggressive forces within the barrel are manipulated by adjusting the turret's rotational speed and the barrel's media level. This gives operators the control necessary to eliminate damage on soft parts such as the aligners 136.

After tumbling to remove sharp edges, the aligner 136 is provided into an ultrasonic washer which disinfects and heat-dries the aligners. A variety of ultrasonic washers can be used as ultrasonic cavitation is able to clean right down to the surface of a part and beyond. It is also able to reach internal areas which are not accessible using other cleaning means including spray and mechanical agitation. The forceful nature of ultrasonic energy provides the physical "push" required to break the mechanical curd ionic bonds that hold very small particles to surfaces. Consistent cleanliness is assured by the ability of ultrasonic energy to reach any surface in contact with the cleaning liquid, which in one embodiment is soap/water combination.

Next, the aligners 136 are packed, and labels are applied to the packages. The resulting packages are then shipped to customers. Typically the appliances are to be worn in a particular sequence to provide desired treatment, such as a progressive movement of teeth through a variety of arrangements to a final desired arrangement. In one embodiment, a system of dental appliances is provided, comprising a plurality of dental appliances wherein at least some of the plurality include non-numeric indicia designating all order in which each of the at least some of the plurality are to be worn by a patient to provide dental treatment. Typically, each of the plurality of dental appliances comprises a polymeric shell having cavities shaped to receive and resiliently reposition teeth from one arrangement to a successive arrangement. In some embodiments, each of the polymeric shells has at least one terminal tooth cavity, and the indicia comprise a terminal tooth cavity of differing length in each of the polymeric shells. In other embodiments, each of the polymeric shells has a height, and the indicia comprise a different height in each of the polymeric shells. In still other embodiments, the indicia comprise one or more cutouts so that each polymeric shell has a different cutout pattern. Sometimes the cutout comprises a notch in an edge of the appliance. In yet other embodiments, the indicia comprise a color wherein each appliance has a different color. The color of the appliances may have the same hue and vary by intensity, for example. The color may comprise a dissolvable dye. Or, the system may further comprise a wrapper removably attachable to each of the appliances, wherein each wrapper has the color. In another embodiment, a system of packaged dental appliances is provided comprising a plurality of packages each containing a dental appliance, wherein the plurality of packages are joined in a continuous chain designating an order in which each of the dental appliances are to be worn by a patient to provide dental treatment. In some instances, the packages are each joined by a perforation wherein the packages can be separated by breaking the perforation. In other instances, the packages are joined by, for example, a heat seal. Further, the system may include a marking on a package at an end of the chain indicating the dental appliance to be worn first. Again, each of the plurality of dental appliances may comprise a polymeric shell having cavities shaped to receive and resiliently reposition teeth from one arrangement to a successive arrangement. In yet other embodiments, a system of dental appliances is provided comprising a plurality of dental appliances to be worn by a patient to provide dental treatment, and a framework, wherein each of the plurality of dental appliances is removably attached to a portion of the framework. In some embodiments, each of the plurality of dental appliances comprises a polymeric shell having cavities shaped to receive and resiliently reposition teeth from one arrangement to a successive arrangement. Further, the system may comprise at least one marking on the framework indicating the order in which the appliances are to be worn by a patient. In still another embodiment, a plurality of packages are produced wherein each of the packages includes a polymeric shell having cavities shaped to receive and resiliently reposition teeth from one arrangement to a successive arrangement, the plurality of package including a first package containing a first shell to be worn by the patient to reposition the teeth from the one arrangement to the successive arrangement and a second package containing a second shell to be worn by the patient to reposition the teeth from the successive arrangement to another successive arrangement. The first package can be provided to the patient at a designated time though a remote delivery system, and delivering the second package to the patient at a later designated time through the remote delivery system. In most embodiments, the remote delivery system comprises a mail delivery system.

Figure 8:
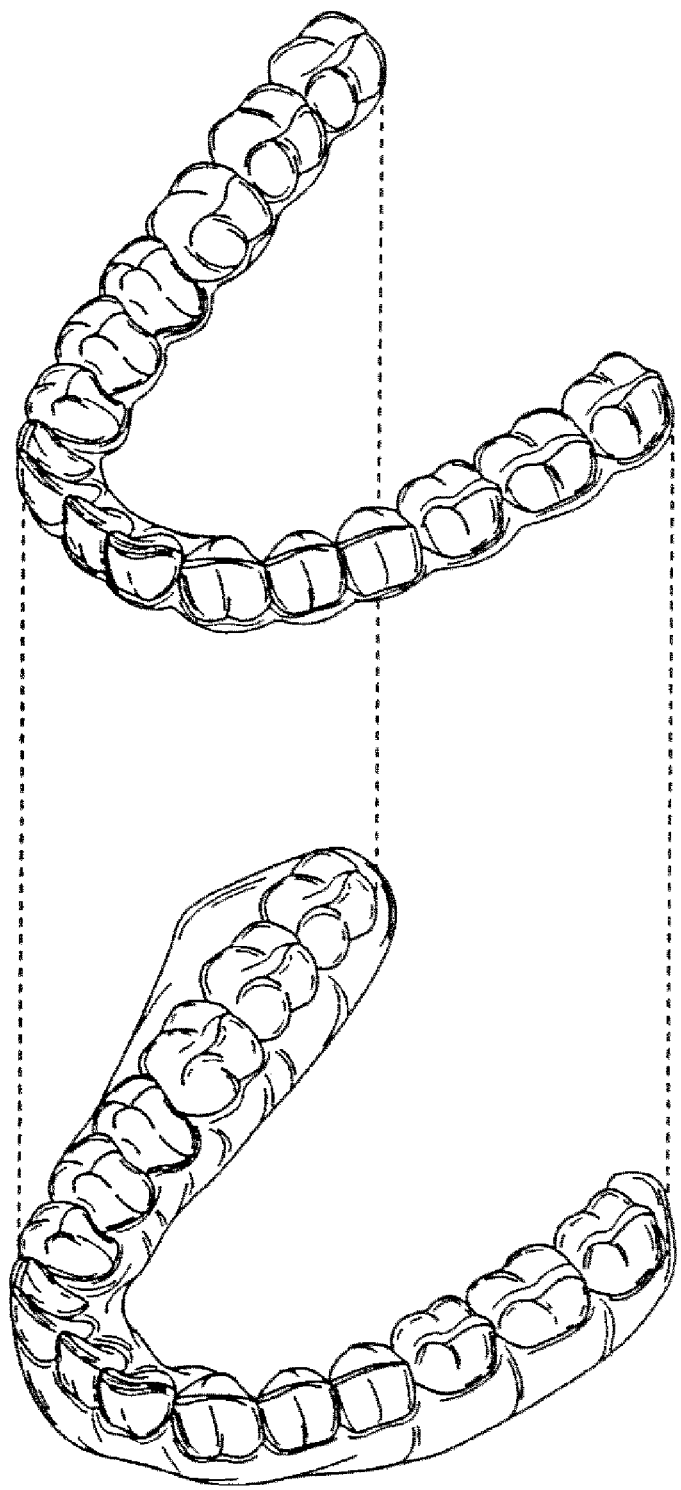
FIG. 8 shows an exemplary dental appliance during use.

FIG. 8 shows an exemplary dental appliance during use. A plurality of incremental position adjustment appliances, one of which is shown in FIG. 8, are used to effect incremental repositioning of individual teeth. In a broadest sense, the system can employ any of the known positioners, retainers, or other removable appliances which are known for finishing and maintaining teeth positions in connection with conventional orthodontic treatment. A plurality of such appliances intended to be worn by a patient successively in order to achieve the gradual tooth repositioning as described herein. The appliance of FIG. 8 is a polymeric shell having a cavity shaped to receive and resiliency reposition teeth from one tooth arrangement to a successive tooth arrangement. The polymeric shell will preferably, but not necessarily, fit over all teeth present in the upper or lower jaw. Often, only certain one(s) of the teeth will be repositioned while others of the teeth will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth which are moved can also serve as a base or anchor region for holding the repositioning appliance.

Additionally, the gums and/or the palette can serve as an anchor region, thus allowing all or nearly all of the teeth to be repositioned simultaneously.

The manner of usage and operation of the invention described above being readily apparent from the above disclosure, no further discussion relative to the manner of usage and operation of the invention shall be provided. With respect to the above description, it is to be understood that the optimum dimensional relationships for the parts of the invention, as well as variations in size, materials, shape, form, function, and manner of operation, assembly, and use, and equivalents of all the foregoing, are apparent to one skilled in the art. Such equivalents are intended to be encompassed by the present invention. Therefore, the foregoing is considered as illustrative only of the principles of the invention. Further, since numerous modifications and changes will be readily apparent to those skilled in the art, it is not intended to limit the invention to the exact construction and operation shovel and described, but to encompass all suitable modifications and equivalents within the scope of the invention. The scope of the invention is indicated by the appended claims rather than by the foregoing description.

What is claimed is:

1. A system for forming molded items from thermoplastic workpieces, comprising:
   a workpiece heating mechanism operable to heat a series of thermoplastic workpieces;
   a workpiece manipulator operable to move each workpiece sequentially from the heating mechanism to a workpiece operation chamber;
   a plurality of molds, each single mold in the plurality of molds representing a unique shape;
   a plug in the workpiece operation chamber that is cooperatively engageable with each of the molds; and
   a mold manipulator operable to sequentially move the plurality of molds to the workpiece operation chamber for engagement with the plug therein;
   the workpiece manipulator and the mold manipulator being operable to position each workpiece in the workpiece operation chamber between a single mold and the plug so that each workpiece is formed into a uniquely shaped molded item through the cooperative engagement of the single mold and the plug.

2. The system of claim 1, further comprising a workpiece introduction system operable to introduce the series of workpieces sequentially into the workpiece heating mechanism.

3. The system of claim 2, wherein the workpiece introduction system is an inline system.

4. The system of claim 2, wherein the workpiece introduction system is a rotary turret system.

5. The system of claim 1, wherein the mold manipulator system is a rotary turret system.

6. The system of claim 2, wherein the workpiece introduction system includes a cutter that is operable to form the series of workpieces from a roll of thermoplastic material.

7. The system of claim 1, further comprising a mold preparation chamber, and wherein the mold manipulator system is operable to move each of the molds from the mold preparation chamber to the workpiece operation chamber.

8. The system of claim 7, wherein the mold preparation chamber includes the mold heating mechanism.

9. The system of claim 1, further comprising a laser-marking system operable to mark each molded item following its removal from the workpiece operation chamber.

10. The system of claim 1, further comprising a trimming system operable to trim each molded item following its removal from the workpiece operation chamber.

11. The system of claim 10, wherein the trimming system includes a multiple-axis CNC system.

12. The system of claim 1, wherein the molded items are uniquely shaped dental aligners.

13. The system of claim 1, wherein the plug is one of a series of plugs, each of which is configured for cooperation with a corresponding mold to ensure that the workpiece is pulled over the mold.

14. A system for forming molded items from thermoplastic workpieces, comprising:
   a workpiece heating mechanism operable to heat a series of thermoplastic workpieces;
   a workpiece operation chamber;
   a workpiece manipulator operable to move the series of workpieces sequentially from the heating mechanism to the workpiece operation chamber;
   a plurality of molds, each single mold in the plurality of molds representing a unique shape; and
   a mold manipulator operable to sequentially move the plurality of molds to the workpiece operation chamber;
   the workpiece manipulator and the mold manipulator being operable to deliver each single workpiece in the series of workpieces and each single mold in the plurality of molds substantially simultaneously to the workpiece operation chamber and to present the single workpiece to the single mold so that the single workpiece is formed into a uniquely shaped molded item.

15. The system of claim 14, further comprising a workpiece introduction system operable to introduce the series of workpieces sequentially into the workpiece heating mechanism.

16. The system of claim 15, wherein the workpiece introduction system is an inline system.

17. The system of claim 15, wherein the workpiece introduction system is a rotary turret system.

18. The system of claim 14, wherein the mold manipulator system is a rotary turret system.

19. The system of claim 15, wherein the workpiece introduction system includes a cutter that is operable to form the series of workpieces from a roll of thermoplastic material.

20. The system of claim 14, further comprising a mold preparation chamber, and wherein the mold manipulator system is operable to move each of the molds from the mold preparation chamber to the workpiece operation chamber.

21. The system of claim 20, wherein the mold preparation chamber includes the mold heating mechanism.

22. The system of claim 14, further comprising a laser-marking system operable to mark each molded item following its removal from the workpiece operation chamber.

23. The system of claim 14, further comprising a trimming system operable to trim each molded item following its removal from the workpiece operation chamber.

24. The system of claim 23, wherein the trimming system includes a multiple-axis CNC system.

25. The system of claim 14, wherein the molded items are uniquely shaped dental aligners.

26. The system of claim 14, wherein the workpiece operation chamber is operable to apply a vacuum to form the single workpiece into the unique mold item.

* * * * *